United States Patent
Asai et al.

(10) Patent No.: US 6,949,263 B2
(45) Date of Patent: Sep. 27, 2005

(54) METHOD FOR PREPARING NICOTIANAMINE OR NICOTIANAMINE-CONTAINING PRODUCT

(75) Inventors: Shouji Asai, Chiba (JP); Akio Obata, Chiba (JP); Emiko Yamazaki, Chiba (JP); Emiko Kinoshita, Chiba (JP); Mamoru Kikuchi, Chiba (JP)

(73) Assignee: Kikkoman Corporation, Chiba (JP)

( * ) Notice: Subject to any disclaimer, the term of this patent is extended or adjusted under 35 U.S.C. 154(b) by 0 days.

(21) Appl. No.: 10/011,490

(22) Filed: Dec. 11, 2001

(65) Prior Publication Data

US 2002/0122857 A1 Sep. 5, 2002

(30) Foreign Application Priority Data

Dec. 11, 2000 (JP) ........................................ 2000-375403

(51) Int. Cl.⁷ ................................................ A61K 35/78
(52) U.S. Cl. ........................................ 424/757; 424/725
(58) Field of Search .................................. 424/757, 725

(56) References Cited

U.S. PATENT DOCUMENTS 4,091,120 A * 5/1978 Goodnight, Jr. et al.
5,792,503 A * 8/1998 Gugger et al.

FOREIGN PATENT DOCUMENTS

| JP | A 63-87990 | | 4/1988 |
| JP | 63-87990 A | | 4/1988 |
| JP | 04-261122 | * | 4/1992 |
| JP | A 5-246865 | | 9/1993 |
| JP | 5-246865 A | | 9/1993 |
| JP | 405246865 A | * | 10/1993 |

OTHER PUBLICATIONS

How et al. (Removal of Phenolic Compounds from Soy Protein Extracts Using Activated Carbon, Journal of Food Science, Vo. 47 (1982), pp. 993–940).*

* cited by examiner

*Primary Examiner*—Brenda Brumback
*Assistant Examiner*—Randall Winston
(74) *Attorney, Agent, or Firm*—Young & Thompson

(57) ABSTRACT

Precipitation fractionation of an aqueous extract of soybeans by addition of an organic solvent such as ethanol or molecular weight fractionation of the extract by ultrafiltration or size exclusion chromatography is appropriately combined with activated carbon filtration, cation- or anion-exchange resin treatment or other adsorbent (e.g., polyamide or octadecylsilica) treatment to provide a nicotianamine product of desired purity. The product is added to food and drink to provide health foods.

3 Claims, No Drawings

METHOD FOR PREPARING NICOTIANAMINE OR NICOTIANAMINE-CONTAINING PRODUCT

BACKGROUND OF THE INVENTION

1. Field of the Invention

The present invention relates to a method for preparing nicotianamine or a nicotianamine-containing product which has angiotensin converting enzyme (ACE) inhibitory activity from an aqueous extract of soybeans and to a health food containing the nicotianamine-containing product as a functional ingredient.

2. Description of the Related Art

Nicotianamine has blood pressure lowering action based on ACE inhibition. Nicotianamine is widely found in the vegetable world, such as tobaccos, rice plants, Chinese matrimony vines, and beeches, and are obtainable from the leaves of these plants (JP-A-63-87990). It is known that nicotianamine is also found in kidney beans and soybeans and that an extract of the beans with water or hot water is treated with a synthetic resin to obtain purified nicotianamine (JP-A-5-246865).

However, the method of obtaining nicotianamine through extraction of plant leaves meets difficulty in stably securing a large quantity of the plant. Since production of kidney beans is very low, it tends to be difficult to procure a stable supply as a raw material of nicotianamine.

On the other hand, soybeans are stably supplied. However, where nicotianamine is prepared from an aqueous extract of soybeans, such as a boiling waste liquid or a soaking waste liquid in the soybean processing industry, by adsorption and desorption by a synthetic resin, the yield is low, resulting in a high cost.

SUMMARY OF THE INVENTION

The inventors studied seeking a method of efficiently preparing nicotianamine from soybeans or soybean materials. As a result they have found that addition of an organic solvent to an aqueous extract of soybeans results in formation of a precipitate, which contains nicotianamine in a high concentration and that a fraction collected from an aqueous extract of soybeans which has a molecular weight of 1,000 or less contains nicotianamine in a high concentration. They have also found that nicotianamine can be obtained with an economic advantage by utilizing, as an aqueous extract, soybean whey which is by-produced in the production of soybean protein isolate.

Based on these findings, the present invention provides a method of preparing nicotianamine comprising adding an organic solvent to an aqueous extract of soybeans and purifying the resulting precipitate and a method of preparing a nicotianamine-containing product comprising adding an organic solvent to an aqueous extract of soybeans and collecting the resulting precipitate as a crude product. The present invention also provides a method of preparing nicotianamine or a nicotianamine-containing product comprising subjecting an aqueous extract of soybeans to ultrafiltration or size exclusion chromatography to collect a fraction having a molecular weight of 1,000 or less. The present invention further provides a method for preparing a nicotianamine-containing product having a nicotianamine content of 0.3% by weight or more which comprises subjecting an aqueous extract of soybeans to ultrafiltration or size exclusion chromatography, collecting a fraction having a molecular weight of 1,000 or less, adding an organic solvent to the fraction, and collecting the resulting precipitate. The present invention furthermore provides a health food containing the nicotianamine-containing product as a functional ingredient.

According to the methods of the present invention, nicotianamine or a nicotianamine-containing product having ACE inhibitory activity is prepared efficiently from an aqueous extract of soybeans, particularly soybean whey. The resulting nicotianamine or nicotianamine-containing product can be taken as such as a health food or be added to foods to provide health foods for treating or preventing symptoms of hypertension.

DETAILED DESCRIPTION OF THE PREFERRED EMBODIMENTS

Soybeans which can be used in the present invention include whole soybeans, skinned soybeans, ground soybeans, and defatted soybeans used as a raw material of soy sauce. The aqueous soybean extract includes an extract of soybeans with water or hot water, a waste liquid used for soaking soybeans, a waste liquid used for boiling soybeans in the soybean processing industry, soybean whey by-produced in the manufacture of soybean protein isolate, and soybean whey by-produced in the manufacture of tofu (soybean curd).

The aqueous soybean extract may be used as such, but it is advisable to previously remove dissolved proteins because the proteins may cause reduction in purity or ACE inhibitory activity of nicotianamine. The proteins can be removed in a conventional manner, for example, by adjusting the pH of the extract to about 4.5 to cause them to precipitate.

A suitable aqueous extract of soybeans is prepared by soaking soybeans in 1 to 20 times their weight of water or hot water for at least 5 minutes, preferably 1 to 20 hours. The extraction is preferably conducted at pH 7 to 9 for extraction efficiency.

An acid is added to the resulting aqueous extract to adjust the pH value to about 4.5, and the extract is centrifuged to remove the precipitate. The supernatant is a preferred material. It is particularly advantageous from the standpoint of utilization of resources to use soybean whey which is by-produced in the production of soybean protein isolate and has mostly been discarded.

If desired, the aqueous soybean extract is concentrated, and an organic solvent is added thereto. A water-soluble organic solvent, such as methanol, ethanol, and acetone, is used. Ethanol is particularly preferred. The organic solvent is preferably added in a concentration of 30% (by weight, hereinafter the same) or more, particularly 50% or more, while the amount varies depending on the degree of concentration of the extract.

Upon addition of the organic solvent, a precipitate is formed in the aqueous extract, which is then collected by an appropriate means, such as centrifugation. The soybean aqueous extract concentrated to a higher degree tends to form a precipitate easier at a lower concentration of the organic solvent. For example, where soybean whey obtained by extraction with 10 times the weight of water is used as such, a suitable organic solvent concentration is 70 to 90%, while a 3- to 4-fold concentrate of the whey produces a sufficient precipitate at an organic solvent concentration of 50 to 60%.

The precipitate as collected, which contains nicotianamine in a high concentration, is dried to powder by vacuum drying, lyophilization, or spray drying to obtain a nicotianamine crude product, which can further be purified to provide a nicotianamine purified product.

It might be conceivable to directly dry an aqueous extract of soybeans, such as whey, to powder, but this involves disadvantages arising from various substances dissolved in the extract such that the resulting nicotianamine product has nicotianamine of low purity, and the extract is difficult to dry to powder or fails to provide satisfactory powder.

The crude nicotianamine product can be purified by, for example, the method described in JP-A-5-246865, Example 2. The physicochemical properties of the nicotianamine thus prepared are as described in JP-A-5-246865, paragraph 0014.

Impurities can further be reduced by treating the aqueous soybean extract by ion-exchange resin treatment, activated carbon filtration or adsorbent treatment or a combination thereof either before or after the organic solvent addition.

Being ampholytic, nicotianamine can be treated with either a cation-exchange resin or an anion-exchange resin. Since nicotianamine has high polarity and is thereby substantially inert to activated carbon, treatment with activated carbon removes oligosaccharides or like impurities present in soybean whey. To remove organic matter of relatively low polarity, such as isoflavons and saponins, the extract can be treated with octadecylsilica, polyamide, synthetic adsorbents (e.g., Diaion HP-20, available from Mitsubishi Chemical Corp.), etc.

Nicotianamine, the molecular weight of which is 303, is able to pass through an ultrafiltration membrane having a molecular weight cut-off of about 1,000 even when it is in the form of a salt. When subjected to size exclusion chromatography, it can be collected in a fraction of molecular weight 1,000 or less. Therefore, it is also possible to recover nicotianamine or a nicotianamine-containing product from an aqueous soybean extract such as soybean whey by ultrafiltration or size exclusion chromatography to collect a fraction having a molecular weight of 1,000 or less.

Nicotianamine or a nicotianamine-containing product with higher purity can be obtained by treating the aqueous soybean extract by ion-exchange resin treatment, activated carbon filtration or adsorbent treatment or a combination thereof either before or after ultrafiltration or size exclusion chromatography as described above.

The nicotianamine-containing product of the present invention can be desalted by electrodialysis or a like means. The dialyzate, which contains nicotianamine in a high concentration, is dried to powder by vacuum drying, lyophilization or spray drying to obtain a crude nicotianamine product, which can further be purified by the above-mentioned purification techniques to prepare a purified nicotianamine product. Purification can be effected to a desired degree according to the intended use of the product.

The above-described method comprising adding an organic solvent and the method comprising ultrafiltration or size exclusion chromatography can be combined to provide a nicotianamine-containing product having a nicotianamine content of 0.3% or more. In this case, also, the above-described treatment with an ion-exchange resin, activated carbon or an adsorbent or a combination thereof can be performed either before or after addition of an organic solvent or either before or after ultrafiltration or size exclusion chromatography. For example, an aqueous soybean extract, preferably soybean whey, is treated by activated carbon filtration, and the filtrate is subjected to ultrafiltration or size exclusion chromatography to harvest a fraction having a molecular weight of 1,000 or smaller. An organic solvent is then added to the fraction in a concentration of 30%, and the precipitate thus formed is collected to give a nicotianamine-containing product having a nicotianamine content of 0.3% or more.

The present invention also provides a health food containing the nicotianamine or nicotianamine-containing product (a crude product or a purified product) obtained by the method of the invention as a functional ingredient. For example, the crude nicotianamine-containing product is mixed with common vehicles and punched into tablets or incorporated into a variety of foods and beverages, such as bakery products (e.g., bread, cake, and cookies), noodles (e.g., buckwheat noodle, wheat noodle, and Chinese noodle), cooked foods (e.g., tempura or deep-fried foods), soybean foods (e.g., tofu and natto (fermented soybeans)), juice, coffee, cocoa, woolong tea, green tea, and health drinks, to make functional food and drink having antihypertensive activity of nicotianamine.

The present invention will now be illustrated in greater detail with reference to Examples. Unless otherwise noted, all the percents and parts are by weight.

EXAMPLE 1

To 400 g of defatted soybean meal was added 5 l of water, and water was adjusted to pH 9. After 90-minute soaking at 25° C., the soybean meal was separated to obtain 4.7 l of the aqueous extract. The extract was adjusted to pH 4.5 and centrifuged at 7500 G for 30 minutes to obtain 4.5 l of the supernatant liquid (soybean whey). Ethanol was added to the whey to a concentration of 80%, followed by centrifugation at 4° C. and at 7500 G for 30 minutes. The collected precipitate was lyophilized to give 12 g of a crude nicotianamine product as white powder, which was found to have a nicotianamine content of 0.5%.

EXAMPLE 2

To 4.5 l of soybean whey prepared in the same manner as in Example 1 was added 150 g of activated carbon (Shirasagi, available from Takeda Chemical Industries, Ltd.), and the mixture was stirred at room temperature for 3 hours to have impurities adsorbed onto the activated carbon. Into the mixture was mixed 150 g of a diatomite filter aid (Radiolite 500), and the mixture was filtered by suction through filter paper No. 2. The filtrate was treated through a hollow fiber type ultrafiltration membrane module having a molecular weight cut-off of 1,000 (Prepscale UF Cartridge, PLAC type, available from Nihon Millipore K.K.). The ultrafiltrate was lyophilized to give 30 g of a white powder, which was found to have a nicotianamine content of 0.3%.

EXAMPLE 3

The powder obtained in Example 2 was re-dissolved in 200 ml of distilled water, and ethanol was added to a concentration of 80%. The ethanol solution was centrifuged at 4° C. and at 7500 G for 30 minutes. The collected solid was lyophilized to obtain 5.4 g of a crude nicotianamine product as a white powder, which contained 1.0% of nicotianamine.

EXAMPLE 4

The ultrafiltrate obtained in Example 2 was passed through a 1-l column of an anion-exchange resin (Diaion PA318, OH⁻ form, available from Mitsubishi Chemical Corp.). The column was washed with 2 l of distilled water and eluted with 2 l of 0.5N hydrochloric acid. The eluate was further passed through a 1-l column of a cation-exchange resin (Dowex 50W×2, H⁺ form, available from the Dow Chemical Co.), and the column was washed with 2 l of distilled water and eluted with 0.5% aqueous ammonia. The fraction of from 2 l up to 3 l was collected and concentrated to 10 ml on a rotary evaporator. The concentrate was lyophilized to give 100 mg of a white powder, which had a nicotianamine content of 40%.

EXAMPLE 5

The nicotianamine-containing powder obtained in Example 4 was dissolved in a small amount of water, and the solution was passed through a 0.5-l column of polyamide C-200 (available from Wako Pure Chemical Industries, Ltd.) pre-equilibrated with 100% ethanol and eluted successively with a 1 liter portion each of 100% ethanol, 90% ethanol, 80% ethanol, 70% ethanol, 60% ethanol and 50% ethanol. The eluate with 70% ethanol, 60% ethanol and 50% ethanol was concentrated, filtered, and lyophilized to give 40 mg of a white powder, which was found to have a nicotianamine content of 80%.

EXAMPLE 6

Two liters of water was added to 400 g of a waste soybean boiling liquid and the obtained mixture was kept at 25° C. for 90 minuets. The insoluble materials were removed by centrifugation to leave 1.9 l of the supernatant liquid. Ethanol was added to the liquid in a concentration of 80%, and the mixture was centrifuged at 4° C. and at 7500 G for 30 minutes. The separated precipitate was lyophilized to give 4 g of a crude nicotianamine product as a white powder, which was found to have a nicotianamine content of 0.15%.

EXAMPLE 7

The following components were mixed up uniformly into granules and punched in a conventional manner to prepare tablets each weighing 500 mg.

| | |
|---|---|
| Crude nicotianamine powder prepared in Example 1 | 300 g |
| Lactose | 100 g |
| Crystalline cellulose | 93 g |
| Talc | 5 g |
| Carboxymethyl cellulose | 2 g |

EXAMPLE 8

The following components were compounded and baked to make cake in a usual manner.

| | |
|---|---|
| Wheat flour | 100 parts |
| Egg | 100 parts |
| Sugar | 100 parts |
| Crude nicotianamine powder prepared in Example 1 | 3 parts |
| Water | 40 parts |

The cake was satisfactory in palatability and flavor with no difference from one containing no nicotianamine product in both texture and appearance.

EXAMPLE 9

The crude nicotianamine powder prepared in Example 1 was added to a commercially available carbonized beverage in a concentration of 1%. It dissolved quickly, and the resulting beverage presented no change in flavor.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application No. 2000-375403 filed Dec. 11, 2000, which is incorporated herein by reference.

What is claimed is:

1. A method of preparing a nicotianamine-containing product having a nicotianamine content of 0.3% by weight or more which comprises subjecting an aqueous extract of soybeans to ultrafiltration or size exclusion chromatography to collect a fraction having a molecular weight of 1,000 or less, adding an organic solvent to the fraction, and collecting the resulting precipitate.

2. The method of preparing a nicotianamine-containing product according to claim 1, which further comprises subjecting the aqueous extract or the fraction to at least one treatment selected from the group consisting of an ion-exchange resin treatment and activated carbon filtration.

3. A method of preparing a nicotianamine-containing product having a nicotianamine content of 0.3% by weight or more which comprises subjecting an aqueous extract of soybeans to activated carbon filtration, subjecting the filtrate to ultrafiltration or size exclusion chromatography to collect a fraction having a molecular weight of 1,000 or less, adding an organic solvent to the fraction in a concentration of 30% by weight or more, arid collecting the resulting precipitate.

* * * * *